United States Patent
Ryokawa et al.

(10) Patent No.: US 7,319,158 B2
(45) Date of Patent: Jan. 15, 2008

(54) PROCESS FOR PRODUCING HIGH-PURITY HAFNIUM AMIDE

(75) Inventors: Atsushi Ryokawa, Ube (JP); Shuhei Yamada, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 11/705,524

(22) Filed: Feb. 13, 2007

(65) Prior Publication Data

US 2007/0197809 A1    Aug. 23, 2007

(30) Foreign Application Priority Data

Feb. 20, 2006 (JP) .............................. 2006-042934
Nov. 20, 2006 (JP) .............................. 2006-312847
Jan. 10, 2007 (JP) .............................. 2007-002547

(51) Int. Cl.
*C07F 7/00* (2006.01)

(52) U.S. Cl. ..................................................... 556/51
(58) Field of Classification Search .................. 556/51
See application file for complete search history.

(56) References Cited

U.S. PATENT DOCUMENTS

2006/0193979 A1* 8/2006 Meiere et al. .............. 427/226

FOREIGN PATENT DOCUMENTS

JP        2005-263771 A     9/2005
JP        2005-298467 A    10/2005

OTHER PUBLICATIONS

Dennis M. Hausmann et al., "Atomic Layer Deposition of Hafnium and Zirconium Oxides Using Metal Amide Precursors", Chem. Mater. 2002, vol. 14, No. 10, pp. 4350-4358.
T. Otsuka, "Journal of the Mining Institute of Japan", 1969, pp. 993-999 (1969).

* cited by examiner

*Primary Examiner*—Porfirio Nazario-Gonzalez
(74) *Attorney, Agent, or Firm*—Crowell & Moring LLP

(57) ABSTRACT

A process for producing a high-purity hafnium amide includes the steps of (a) adding a compound which contains a carbonyl group or sulfonyl group and is represented by the formula of $A(O_yXO_nR_f)_m$ (e.g., $CF_3SO_3H$, $Hf(CF_3SO_3)_4$, $(CF_3SO_2)_2O$, $CF_3CO_2H$, $CH_3SO_3H$, $C_6H_5SO_3H$, and $(CH_3SO_2)_2O$), to a crude hafnium amide which is represented by the formula of $Hf[N(R_1)(R_2)]_4$, where each of $R_1$ and $R_2$ independently represents a methyl group or ethyl group, and which contains a zirconium component as an impurity; and (b) subjecting a product of the step (a) to a distillation under reduced pressure, thereby removing the zirconium component from the crude hafnium amide.

10 Claims, No Drawings

PROCESS FOR PRODUCING HIGH-PURITY HAFNIUM AMIDE

BACKGROUND OF THE INVENTION

The present invention relates to a process for producing a high-purity hafnium amide (e.g., tetrakis(diethylamido) hafnium $Hf[N(C_2H_5)_2]_4$) as a hafnium complex, which is preferable as a film-formation raw material in the semiconductor production. Specifically, hafnium amide can be used as a thin-film material for forming a gate insulating film of large-scale integrated circuits (LSI) or the like in metal organic chemical vapor deposition (MOCVD) process.

Hafnium amide as a hafnium complex is relatively high in volatility, and its uses have expanded in recent years as a raw material for forming a hafnium thin film of semiconductor gate insulating films in MOCVD processes. Since the gate insulating film is positioned at the bottom of a semiconductor, it is required to have an extremely high-purity film composition. Thus, the hafnium amide for that is also required to be a high-purity product.

In general, hafnium amide is produced by using hafnium tetrachloride as a raw material. Of impurities contained in hafnium amide, zirconium component, which is derived from this raw material, is generally contained in a high concentration of about 1,000-5,000 weight ppm (wtppm). Since hafnium and zirconium belong to the same group of the periodic table and have analogous chemical properties due to lanthanide contraction, it is difficult to separate hafnium and zirconium from each other. Therefore, zirconium component is generally contained in the above-mentioned high concentration in hafnium amide.

Zirconium component contained in a hafnium amide is a zirconium amide having the same ligands as those of the hafnium amide. Tetrakis(diethylamido)hafnium, for example, produced by using hafnium tetrachloride and lithium diethylamide as raw materials contains tetrakis(diethylamido)zirconium as a zirconium component, which is derived from zirconium tetrachloride contained in the hafnium tetrachloride. Since tetrakis(diethylamido)hafnium and tetrakis(diethylamido)zirconium have almost no difference in vapor pressure and have similar chemical properties, their separation is difficult by a simple procedure, such as simple distillation under reduced pressure (see D. M. Hausmann et al., "Chem. Mater.", Vol. 14, No. 10, 4350-4358 (2002)).

T. Otsuka, "Journal of the Mining Institute of Japan" (written in Japanese with English abstract at the last page) pages 993-999 (1969) proposes a zirconium and hafnium separation by liquid-liquid extraction with hexone (methyl isobutyl ketone). This separation is high in running costs, since recovery of the solvent and the reagents used is inferior. Furthermore, it is difficult to apply the separation to hafnium amide, which has a hydrolysis tendency, since the separation uses an extraction distribution coefficient difference between water and hexone.

Japanese Patent Laid-open Publication 2005-298467 discloses a process for purifying a hafnium amide, tetrakis(dimethylamido)hafnium, by removing zirconium component through a fractional distillation under reduced pressure. The hafnium amide of this publication is limited to tetrakis(dimethylamido)hafnium due to the relation of vapor pressure difference between hafnium component and zirconium component. In other words, the process of this publication cannot be applied to the purifications of other hafnium amides, such as tetrakis(ethylmethylamido)hafnium and tetrakis(diethylamido)hafnium.

Japanese Patent Laid-open Publication 2005-263771 discloses a process for producing a high-purity tetrakis(dialkylamino)hafnium by the steps of (a) reacting hafnium tetrachloride with a dialkylaminolithium in an organic solvent having a water content of 100 ppm or less, under an inert gas atmosphere; and (b) subjecting a crude tetrakis(dialkylamino)hafnium obtained by the step (a) to fractional distillation.

SUMMARY OF THE INVENTION

It is an object of the present invention to easily and safely remove zirconium component from a crude hafnium amide (a hafnium complex), thereby producing a high-purity hafnium amide with high yield.

According to the present invention, there is provided a process for producing a high-purity hafnium amide; including the steps of:

(a) adding a compound which contains a carbonyl group or sulfonyl group and is represented by the formula of $A(O_yXO_nR_f)_m$, where A represents a hydrogen atom, oxygen atom or hafnium atom, where X represents a carbon atom or sulfur atom when A represents a hydrogen atom or oxygen atom, where X represents a sulfur atom when A represents a hafnium atom, where each of m, n and y represents 1 when A and X respectively represent a hydrogen atom and a carbon atom, thereby providing the formula of $R_fCO_2H$ (e.g., $CH_3CO_2H$ and $CF_3CO_2H$), where m, n and y respectively represent 1, 2 and 1 when A and X respectively represent a hydrogen atom and a sulfur atom, thereby providing the formula of $R_fSO_3H$ (e.g., $CF_3SO_3H$, $CH_3SO_3H$, and $C_6H_5SO_3H$), where m, n and y respectively represent 2, 1 and 0 when A represents an oxygen atom and when X represents a carbon atom, thereby providing the formula of $(R_fCO)_2O$ (e.g., $(CH_3CO)_2O$ and $(CF_3CO)_2O$), where m, n and y respectively represent 2, 2 and 0 when A represents an oxygen atom and when X represents a sulfur atom, thereby providing the formula of $(R_fSO_2)_2O$ (e.g., $(CF_3SO_2)_2O$ and $(CH_3SO_2)_2O$), where m, n and y respectively represent 4, 2 and 1 when A represents a hafnium atom, thereby providing the formula of $Hf(R_fSO_3)_4$ (e.g., $Hf(CF_3SO_3)_4$), where $R_f$ is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A represents a hydrogen atom or oxygen atom, and where $R_f$ is a $C_1$-$C_{12}$ perfluoroalkyl group when A represents a hafnium atom, to a crude hafnium amide which is represented by the formula of $Hf[N(R_1)(R_2)]_4$, where each of $R_1$ and $R_2$ independently represents a methyl group or ethyl group, and which contains a zirconium component as an impurity; and (b) subjecting a product of the step (a) to a distillation under reduced pressure, thereby removing the zirconium component from the crude hafnium amide.

DETAILED DESCRIPTION

By the above process of the present invention, it is possible to easily and safely remove zirconium component from a crude hafnium amide, thereby producing a high-purity hafnium amide with high yield. Furthermore, it is possible by repeating the above process to lower the zirconium component concentration to the extent that is required as that of a high-purity hafnium amide used as a semiconductor film-forming material. With this, it is possible to turn a crude hafnium amide having a zirconium component concentration of 1,000-5,000 weight ppm (wtppm) to a high-purity hafnium amide having a zirconium component concentration of 100 wtppm or less, preferably 10 wtppm or less, more preferably 1 wtppm or less.

The present invention can be applied to the production of a high-purity hafnium amide, which is needed in semiconductor gate insulating film formation and the like. The high-purity hafnium amide obtained by the present invention can be used, for example, as a MOCVD material for forming a high dielectric constant gate insulating film in semiconductor production processes The above-mentioned steps (a) and (b) can be conducted for the purpose of removing zirconium component from a crude hafnium amide having a zirconium component concentration of, for example, 1-5,000 wtppm. With this, the zirconium concentration of the distillate obtained by the step (b) can be reduced by about 1/10 to about 9/10 of the original zirconium concentration of the crude hafnium amide. In contrast, the zirconium concentration is increased in the residue of the distillation of the step (b). It is assumed that zirconium component (zirconium amide complex) of the crude hafnium amide turns into a nonvolatile substance, which is low in vapor pressure, by adding the above compound (e.g., a compound containing a perfluoroalkylsulfonyl group) of the step (a) to the crude hafnium amide.

Specific examples of the compound used in the step (a) include acetic acid, trifluoroacetic acid, benzoic acid, methanesulfonic acid, trifluoromethanesulfonic acid, benzenesulfonic acid, acetic anhydride, trifluoroacetic anhydride, benzoic anhydride, methanesulfonic anhydride, trifluoromethanesulfonic anhydride, benzenesulfonic anhydride, and hafnium trifluoromethanesulfonato. Of these, it is preferable to use trifluoromethanesulfonic acid, which is low in price and effective in action.

The compound of the step (a) may be added in an amount of 1-100 mol %, preferably 5-50 mol %, from the viewpoint of suppressing side reactions with the hafnium amide, relative to mol number (100 mol %) of the zirconium component of the crude hafnium amide.

Heat is generated violently by adding the compound to the crude hafnium amide in the step (a). Therefore, the reaction temperature (i.e., the temperature of the resulting mixture) may be maintained in a range of −78 to +100° C., preferably −78 to +30° C., from the viewpoint of suppressing side reactions.

It is preferable to conduct a stirring of the reaction liquid for 1 to 3 hours from the viewpoint of homogenizing the reaction mixture, after adding the compound to the crude hafnium amide in the step (a) and prior to the distillation under reduced pressure in the step (b).

The distillation of the step (b) may be conducted by normal method, preferably under a pressure of 0.01 to 0.60 kPa. It is possible to sufficiently reduce the zirconium concentration of the crude hafnium amide by conducting a simple distillation under reduced pressure in the step (b), since the addition of the compound in the step (a) is assumed to generate a vapor pressure difference between the zirconium component and the hafnium component, as stated above.

Although the hafnium amide obtained by the step (b) contains a substantially low concentration of zirconium component, it may contain about 0.1-4 wt % of the compound used in the step (a). Thus, the process of the present invention may further include the steps of:

(c) adding a lithium alkylamide represented by the formula of $Li(NR_3R_4)$, where each of $R_3$ and $R_4$ independently represents a methyl group or ethyl group, to a distillate obtained by the step (b); and (d) subjecting a product of the step (c) to a distillation under reduced pressure, thereby removing the compound of the step (a) from the distillate obtained by the step (b). With this, it is possible to avoid lowering of the vaporization stability of the hafnium amide and corrosion of raw material introducing piping in a film-forming process.

It is possible to turn the compound of the step (a) into a nonvolatile compound, such as a perfluoroalkylsulfonyl-containing lithium salt, by adding the lithium alkylamide in the step (c). Then, it is possible to lower the concentration of the compound in the hafnium amide to a concentration less than the detection limit (e.g., 10 wtppm) of ion chromatograph by conducting the distillation of the step (d) to isolate the target hafnium amide. It should be noted that the zirconium concentration of the hafnium amide does almost not change before and after the removal of the compound of the step (a) by the steps (c) and (d).

Specific examples of the lithium alkylamide are lithium dimethylamide, lithium ethylmethylamide, and lithium diethylamide. An alkyl substituent of the lithium alkylamide, which is represented by the formula of $R_3R_4$, can be identical with an alkyl substituent of the hafnium amide of the step (a), which is represented by the formula of $(R_1)(R_2)$. For example, in case that the hafnium amide is tetrakis(diethylamido)hafnium, the lithium alkylamide can be lithium diethylamide. Furthermore, in case that the hafnium amide is tetrakis(dimethylamido)hafnium, the lithium alkylamide can be lithium dimethylamide.

It is preferable to use 1-50 equivalents of the lithium alkylamide in the step (c), relative to one equivalent of the compound contained in the hafnium amide. If it is less than 1 equivalent, the compound may not be reduced sufficiently. Even if it is greater than 50 equivalents, it may be difficult to expect a further reduction of the compound. This is also uneconomic.

The lithium alkylamide is in powdery solid under normal temperature. In the step (c), it is possible to add the lithium alkylamide itself as a solid to the hafnium amide obtained by the step (b). Alternatively, it is possible to dissolve the lithium alkylamide in an organic solvent and then add the resulting solution to the hafnium amide. Examples of this organic solvent include diethyl ether, hexane and toluene, in view of the hafnium amide's solubility, reactivity and the like. Of these, it is preferable to use toluene, which is easily available and low in price.

The temperature upon adding the lithium alkylamide to the hafnium amide in the step (c) may be −78 to +200° C., preferably 0 to +100° C. If it is higher than 200° C., the lithium alkylamide may be pyrolyzed. The distillation of the step (d) may be conducted, immediately after the addition of the lithium alkylamide in the step (c). Alternatively, stirring with a stirrer or the like may be conducted, prior to the distillation of the step (d).

The distillation of the step (d) is conducted for isolating the target hafnium amide. Similar to the distillation of the step (b), this distillation may be conducted by a normal method under reduced pressure, preferably in a range of 0.01 to 0.60 kPa. With this, it is possible to obtain a high-purity hafnium amide, in which the concentration of the compound is less than 10 wtppm. This high-purity hafnium amide can be substantially free from the zirconium component by repeating the steps (a) and (b), prior to conducting the steps (c) and (d), as shown by the results of Examples 16-23.

The following non-limiting examples are illustrative of the present invention.

EXAMPLE 1

A 500 mL, five-necked, glass flask was equipped with a dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium $Hf[N(C_2H_5)_2]_4$ having a zirconium concentration of 1,000 weight ppm (wtppm), followed by cooling to 0° C. and then adding 15.6 g (104 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 66.5 g. This distillate was found by $^1HNMR$ to contain tetrakis(diethylamido)hafnium $Hf[N(C_2H_5)_2]_4$ as a main component. Furthermore, the zirconium concentration of the distillate was measured by inductively coupled plasma (ICP) spectrometry. With this, it was found that the zirconium concentration had decreased from 1,000 wtppm to 138 wtppm. Furthermore, the distillate was found by ion chromatography to have a trifluoromethanesulfonic acid ion concentration of 2.1 wt %. The residue after the distillation was in 35.0 g and had a zirconium concentration of 1,884 wtppm and a trifluoromethanesulfonic acid ion concentration of 29.0 wt %.

EXAMPLE 2

A 500 mL, five-necked, glass flask equipped with a reflux condenser, a thermometer and a stirrer was charged with 65.0 g of the distillate obtained by Example 1. Then, 1.5 g (19 mmol) of lithium diethylamide $LiN(C_2H_5)_2$ were put into the flask, followed by stirring at room temperature for 1 hr. The resulting reaction liquid was subjected to a distillation at 125° C. under 0.12 kPa, thereby obtaining a distillate of 42 g. This distillate was found by $^1HNMR$ to contain tetrakis(diethylamido)hafnium $Hf[N(C_2H_5)_2]_4$ as a main component. Furthermore, the zirconium concentration of the distillate was 115 wtppm. Furthermore, it was found that the trifluoromethanesulfonic acid ion concentration of the distillate had decreased to 10 wtppm or less.

The residue after the distillation was in 19.0 g and had a zirconium concentration of 217 wtppm and a trifluoromethanesulfonic acid ion concentration of 7.2 wt %.

The yield of the obtained high-purity tetrakis(diethylamido)hafnium, based on the crude tetrakis(diethylamido)hafnium having a zirconium concentration of 1,000 wtppm, was 46 wt %.

EXAMPLE 3

A 500 mL, five-necked, glass flask was equipped with a powder dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium $Hf[N(C_2H_5)_2]_4$ having a zirconium concentration of 1,000 wtppm, followed by cooling to 0° C. and then adding 20.0 g (25.8 mmol) of hafnium trifluoromethanesulfonato $Hf(CF_3SO_3)_4$ in a dropwise manner from the powder dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 79.5 g. This distillate was found by $^1HNMR$ to contain tetrakis(diethylamido)hafnium $Hf[N(C_2H_5)_2]_4$ as a main component. Furthermore, the zirconium concentration of the distillate was measured by ICP spectrometry. With this, it was found that the zirconium concentration had decreased from 1,000 wtppm to 198 wtppm. Furthermore, the distillate was found by ion chromatography to have a trifluoromethanesulfonic acid ion concentration of 4.2 wt %. The residue after the distillation was in 31.0 g and had a zirconium concentration of 2,840 wtppm and a trifluoromethanesulfonic acid ion concentration of 28.8 wt %.

EXAMPLE 4

A 500 mL, five-necked, glass flask equipped with a powder dropping funnel, a reflux condenser, a thermometer, and a stirrer was charged with 75.0 g of the distillated obtained by Example 3, followed by cooling to 0° C. and then adding 1.8 g (2 mmol) of hafnium trifluoromethanesulfonato $Hf(CF_3SO_3)_4$ in a dropwise manner from the powder dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 63.9 g. This distillate was found by $^1HNMR$ to contain tetrakis(diethylamido)hafnium $Hf[N(C_2H_5)_2]_4$ as a main component. Furthermore, the zirconium concentration of the distillate was measured by ICP spectrometry. With this, it was found that the zirconium concentration had decreased to 61 wtppm. Furthermore, the distillate was found by ion chromatography to have a trifluoromethanesulfonic acid ion concentration of 1.8 wt %. The residue after the distillation was in 8.7 g and had a zirconium concentration of 1,200 wtppm and a trifluoromethanesulfonic acid ion concentration of 17.0 wt %.

EXAMPLE 5

A 500 mL, five-necked, glass flask equipped with a reflux condenser, a thermometer and a stirrer was charged with 60.0 g of the distillate obtained by Example 4. Then, 4.7 g (59 mmol) of lithium diethylamide $LiN(C_2H_5)_2$ were put into the flask, followed by stirring at room temperature for 1 hr. The resulting reaction liquid was subjected to a distillation at 125° C. under 0.12 kPa, thereby obtaining a distillate of 55.0 g. This distillate was found by $^1HNMR$ to contain tetrakis(diethylamido)hafnium $Hf[N(C_2H_5)_2]_4$ as a main component. Furthermore, the zirconium concentration of the distillate was 48 wtppm. Furthermore, it was found that the trifluoromethanesulfonic acid ion concentration of the distillate had decreased to 10 wtppm or less.

The residue after the distillation was in 3.5 g and had a zirconium concentration of 291 wtppm and a trifluoromethanesulfonic acid ion concentration of 28.5 wt %.

The yield of the obtained high-purity tetrakis(diethylamido)hafnium, based on the crude tetrakis(diethylamido)hafnium having a zirconium concentration of 1,000 wtppm, was 61 wt %.

EXAMPLE 6

A 500 mL, five-necked, glass flask was equipped with a dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium $Hf[N$ $(C_2H_5)_2]_4$ having a zirconium concentration of 733 wtppm, followed by cooling to 0° C. and then adding 29.5 g (104 mmol) of trifluoromethanesulfonic anhydride $(CF_3SO_2)_2O$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 69.5 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased from 733 wtppm to 80 wtppm. Furthermore, the distillate was found by ion chromatography to have a trifluoromethanesulfonic acid ion concentration of 2.4 wt %. The residue after the distillation was in 31.7 g and had a zirconium concentration of 2,112 wtppm and a trifluoromethanesulfonic acid ion concentration of 33.8 wt %.

EXAMPLE 7

A 500 mL, five-necked, glass flask equipped with a reflux condenser, a thermometer and a stirrer was charged with 65.0 g of the distillate obtained by Example 6. Then, 8.8 g (111 mmol) of lithium diethylamide LiN$(C_2H_5)_2$ were put into the flask, followed by stirring at room temperature for 1 hr. The resulting reaction liquid was subjected to a distillation at 125° C. under 0.12 kPa, thereby obtaining a distillate of 49.0 g. This distillate was found by $^1$HNMR to contain tetrakis(diethylamido)hafnium Hf[N$(C_2H_5)_2]_4$ as a main component. Furthermore, the zirconium concentration of the distillate was 66 wtppm. Furthermore, it was found that the trifluoromethanesulfonic acid ion concentration of the distillate had decreased to 10 wtppm or less.

The residue after the distillation was in 7.5 g and had a zirconium concentration of 147 wtppm and a trifluoromethanesulfonic acid ion concentration of 16.7 wt %.

The yield of the obtained high-purity tetrakis(diethylamido)hafnium, based on the crude tetrakis(diethylamido)hafnium having a zirconium concentration of 733 wtppm, was 52 wt %.

EXAMPLE 8

A 500 mL, five-necked, glass flask was equipped with a dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium Hf[N$(C_2H_5)_2]_4$ having a zirconium concentration of 733 wtppm, followed by cooling to 0° C. and then adding 11.9 g (104 mmol) of trifluoroacetic acid $CF_3CO_2H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 58.4 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased from 733 wtppm to 388 wtppm. Furthermore, the distillate was found by ion chromatography to have a trifluoroacetic acid ion concentration of 2.7 wt %. The residue after the distillation was in 26.5 g and had a zirconium concentration of 1,786 wtppm and a trifluoroacetic acid ion concentration of 35.7 wt %.

EXAMPLE 9

A 500 mL, five-necked, glass flask equipped with a reflux condenser, a thermometer and a stirrer was charged with 55.0 g of the distillate obtained by Example 8. Then, 2.1 g (26 mmol) of lithium diethylamide-LiN$(C_2H_5)_2$ were put into the flask, followed by stirring at room temperature for 1 hr. The resulting reaction liquid was subjected to a distillation at 125° C. under 0.12 kPa, thereby obtaining a distillate of 49.0 g. This distillate was found by $^1$HNMR to contain tetrakis(diethylamido)hafnium Hf[N$(C_2H_5)_2]_4$ as a main component. Furthermore, the zirconium concentration of the distillate was 364 wtppm. Furthermore, it was found that the trifluoroacetic acid ion concentration of the distillate had decreased to 10 wtppm or less.

The residue after the distillation was in 3.5 g and had a zirconium concentration of 950 wtppm and a trifluoroacetic acid ion concentration of 41.5 wt %.

The yield of the obtained high-purity tetrakis(diethylamido)hafnium, based on the crude tetrakis(diethylamido)hafnium having a zirconium concentration of 733 wtppm, was 55 wt %.

EXAMPLE 10

A 500 mL, five-necked, glass flask was equipped with a dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium Hf[N$(C_2H_5)_2]_4$ having a zirconium concentration of 733 wtppm, followed by cooling to 0° C. and then adding 10.0 g (104 mmol) of methanesulfonic acid $CH_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 67.2 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased from 733 wtppm to 258 wtppm. Furthermore, the distillate was found by ion chromatography to have a methanesulfonic acid ion concentration of 2.5 wt %. The residue after the distillation was in 27.0 g and had a zirconium concentration of 2,003 wtppm and a methanesulfonic acid ion concentration of 30.6 wt %.

EXAMPLE 11

A 500 mL, five-necked, glass flask equipped with a reflux condenser, a thermometer and a stirrer was charged with 65.0 g of the distillate obtained by Example 10. Then, 2.7 g (34 mmol) of lithium diethylamide LiN$(C_2H_5)_2$ were put into the flask, followed by stirring at room temperature for 1 hr. The resulting reaction liquid was subjected to a distillation at 125° C. under 0.12 kPa, thereby obtaining a distillate of 49.0 g. This distillate was found by $^1$HNMR to contain tetrakis(diethylamido)hafnium Hf[N$(C_2H_5)_2]_4$ as a main component. Furthermore, the zirconium concentration of the distillate was 246 wtppm. Furthermore, it was found that the methansulfonic acid ion concentration of the distillate had decreased to 10 wtppm or less.

The residue after the distillation was in 4.0 g and had a zirconium concentration of 742 wtppm and a methanesulfonic acid ion concentration of 39.7 wt %.

The yield of the obtained high-purity tetrakis(diethylamido)hafnium, based on the crude tetrakis(diethylamido)hafnium having a zirconium concentration of 733 wtppm, was 58 wt %.

EXAMPLE 12

A 500 mL, five-necked, glass flask was equipped with a powder dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium Hf[N(C$_2$H$_5$)$_2$]$_4$ having a zirconium concentration of 3,129 wtppm, followed by cooling to 0° C. and then adding 16.5 g (104 mmol) of benzenesulfonic acid C$_6$H$_5$SO$_3$H in a dropwise manner from the powder dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 70.5 g. This distillate was found by $^1$HNMR to contain tetrakis(diethylamido)hafnium Hf[N(C$_2$H$_5$)$_2$]$_4$ as a main component. Furthermore, the zirconium concentration of the distillate was measured by ICP spectrometry. With this, it was found that the zirconium concentration had decreased from 3,129 wtppm to 1,478 wtppm. Furthermore, the distillate was found by ion chromatography to have a benzenesulfonic acid ion concentration of 0.1 wt %. The residue after the distillation was in 34.0 g and had a zirconium concentration of 6,078 wtppm and a methansulfonic acid ion concentration of 47.4 wt %.

EXAMPLE 13

A 500 mL, five-necked, glass flask equipped with a reflux condenser, a thermometer and a stirrer was charged with 65.0 g of the distillate obtained by Example 12. Then, 0.1 g (1 mmol) of lithium diethylamide LiN(C$_2$H$_5$)$_2$ were put into the flask, followed by stirring at room temperature for 1 hr. The resulting reaction liquid was subjected to a distillation at 125° C. under 0.12 kPa, thereby obtaining a distillate of 62.3 g. This distillate was found by $^1$HNMR to contain tetrakis(diethylamido)hafnium Hf[N(C$_2$H$_5$)$_2$]$_4$ as a main component. Furthermore, the zirconium concentration of the distillate was 1,456 wtppm. Furthermore, it was found that the benzenesulfonic acid ion concentration of the distillate had decreased to 10 wtppm or less.

The residue after the distillation was in 1.8 g and had a zirconium concentration of 2,874 wtppm and a benzenesulfonic acid ion concentration of 3.5 wt %.

The yield of the obtained high-purity tetrakis(diethylamido)hafnium, based on the crude tetrakis(diethylamido)hafnium having a zirconium concentration of 3,129 wtppm, was 67 wt %.

EXAMPLE 14

A 500 mL, five-necked, glass flask was equipped with a powder dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium Hf[N(C$_2$H$_5$)$_2$]$_4$ having a zirconium concentration of 3,129 wtppm, followed by cooling to 0° C. and then adding 18.0 g (104 mmol) of methanesulfonic anhydride (CH$_3$SO$_2$)$_2$O in a dropwise manner from the powder dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 69.0 g. This distillate was found by $^1$HNMR to contain tetrakis(diethylamido)hafnium Hf[N(C$_2$H$_5$)$_2$]$_4$ as a main component. Furthermore, the zirconium concentration of the distillate was measured by ICP spectrometry. With this, it was found that the zirconium concentration had decreased from 3,129 wtppm to 639 wtppm. Furthermore, the distillate was found by ion chromatography to have a methanesulfonic acid ion concentration of 1.7 wt %. The residue after the distillation was in 35.0 g and had a zirconium concentration of 7,580 wtppm and a methanesulfonic acid ion concentration of 25.0 wt %.

EXAMPLE 15

A 500 mL, five-necked, glass flask equipped with a reflux condenser, a thermometer and a stirrer was charged with 65.0 g of the distillate obtained by Example 14. Then, 1.8 g (23 mmol) of lithium diethylamide LiN(C$_2$H$_5$)$_2$ were put into the flask, followed by stirring at room temperature for 1 hr. The resulting reaction liquid was subjected to a distillation at 125° C. under 0.12 kPa, thereby obtaining a distillate of 62.3 g. This distillate was found by $^1$HNMR to contain tetrakis(diethylamido)hafnium Hf[N(C$_2$H$_5$)$_2$]$_4$ as a main component. Furthermore, the zirconium concentration of the distillate was 610 wtppm. Furthermore, it was found that the methanesulfonic acid ion concentration of the distillate had decreased to 10 wtppm or less.

The residue after the distillation was in 1.8 g and had a zirconium concentration of 1,910 wtppm and a methanesulfonic acid ion concentration of 45.1 wt %.

The yield of the obtained high-purity tetrakis(diethylamido)hafnium, based on the crude tetrakis(diethylamido)hafnium having a zirconium concentration of 3,129 wtppm, was 68 wt %.

EXAMPLE 16

A 500 mL, five-necked, glass flask was equipped with a dropping funnel, a reflux condenser, a thermometer, and a stirrer, followed by replacing the inside atmosphere with nitrogen gas. This flask was charged with 100.0 g (214 mmol) of a crude tetrakis(diethylamido)hafnium Hf[N(C$_2$H$_5$)$_2$]$_4$ having a zirconium concentration of 900 wtppm, followed by cooling to 0° C. and then adding 3.5 g (23 mmol) of trifluoromethanesulfonic acid CF$_3$SO$_3$H in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 95.8 g. This distillate was found by $^1$HNMR to contain tetrakis(diethylamido)hafnium Hf[N(C$_2$H$_5$)$_2$]$_4$ as a main component. Furthermore, the zirconium concentration of the distillate was measured by ICP spectrometry. With this, it was found that the zirconium concentration had decreased from 900 wtppm to 492 wtppm. Furthermore, the distillate was found by ion chromatography to have a trifluoromethanesulfonic acid ion concentration of 1.6 wt %. The residue after the distillation was in 6.5 g and had a zirconium concentration of 6,591 wtppm and a trifluoromethanesulfonic acid ion concentration of 28.5 wt %.

EXAMPLE 17

A 500 mL, five-necked, glass flask equipped with a dropping funnel, a reflux condenser, a thermometer, and a stirrer was charged with 90.0 g of the distillate obtained by Example 16, followed by cooling to 0° C. and then adding 3.1 g (21 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 83.9 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 163 wtppm. Furthermore, the distillate was found by ion chromatography to have a trifluoromethanesulfonic acid ion concentration of 1.7 wt %. The residue after the distillation was in 7.2 g and had a zirconium concentration of 4,250 wtppm and a trifluoromethanesulfonic acid ion concentration of 41.1 wt %.

EXAMPLE 18

A 500 mL, five-necked, glass flask equipped with a dropping funnel, a reflux condenser, a thermometer, and a stirrer was charged with 80.0 g of the distillate obtained by Example 17, followed by cooling to 0° C. and then adding 2.8 g (19 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 71.4 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 48 wtppm. Furthermore, the distillate was found by ion chromatography to have a trifluoromethanesulfonic acid ion concentration of 1.4 wt %. The residue after the distillation was in 9.6 g and had a zirconium concentration of 997 wtppm and a trifluoromethanesulfonic acid ion concentration of 31.5 wt %.

EXAMPLE 19

A 500 mL, five-necked, glass flask equipped with a dropping funnel, a reflux condenser, a thermometer, and a stirrer was charged with 65.0 g of the distillate obtained by Example 18, followed by cooling to 0° C. and then adding 2.3 g (15 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 60.2 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 20 wtppm. Furthermore, the distillate was found by ion chromatography to have a trifluoromethanesulfonic acid ion concentration of 1.5 wt %. The residue after the distillation was in 4.6 g and had a zirconium concentration of 413 wtppm and a trifluoromethanesulfonic acid ion concentration of 47.3 wt %.

EXAMPLE 20

A 500 mL, five-necked, glass flask equipped with a dropping funnel, a reflux condenser, a thermometer, and a stirrer was charged with 55.0 g of the distillate obtained by Example 19, followed by cooling to 0° C. and then adding 2.0 g (13 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 49.7 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 6 wtppm. Furthermore, the distillate was found by ion chromatography to have a trifluoromethanesulfonic acid ion concentration of 1.6 wt %. The residue after the distillation was in 5.7 g and had a zirconium concentration of 138 wtppm and a trifluoromethanesulfonic acid ion concentration of 33.2 wt %.

EXAMPLE 21

A 500 mL, five-necked, glass flask equipped with a dropping funnel, a reflux condenser, a thermometer, and a stirrer was charged with 45.0 g of the distillate obtained by Example 20, followed by cooling to 0° C. and then adding 1.6 g (11 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 40.5 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 2 wtppm. Furthermore, the distillate was found by ion chromatography to have a trifluoromethanesulfonic acid ion concentration of 1.6 wt %. The residue after the distillation was in 6.8 g and had a zirconium concentration of 27 wtppm and a trifluoromethanesulfonic acid ion concentration of 23.6 wt %.

EXAMPLE 22

A 500 mL, five-necked, glass flask equipped with a dropping funnel, a reflux condenser, a thermometer, and a stirrer was charged with 35.0 g of the distillate obtained by Example 21, followed by cooling to 0° C. and then adding 1.2 g (8 mmol) of trifluoromethanesulfonic acid $CF_3SO_3H$ in a dropwise manner from the dropping funnel by spending 1 hr. After the dropping, the temperature was raised to 20° C. with stirring for 1 hr. The resulting reaction liquid was subjected to a distillation at 125° C. under 0.12 kPa, thereby obtaining a distillate of 31.1 g. This distillate was found by $^1$HNMR to contain tetrakis(diethylamido)hafnium Hf[N$(C_2H_5)_2]_4$ as a main component. Furthermore, the zirconium concentration of the distillate was measured by ICP spectrometry. With this, it was found that the zirconium concentration had decreased to 0.8 wtppm. Furthermore, the distillate was found by ion chromatography to have a trifluoromethanesulfonic acid ion concentration of 1.5 wt %. The residue after the distillation was in 3.5 g and had a zirconium concentration of 11 wtppm and a trifluoromethanesulfonic acid ion concentration of 34.2 wt %.

EXAMPLE 23

A 500 mL, five-necked, glass flask equipped with a reflux condenser, a thermometer and a stirrer was charged with 25.0 g of the distillate obtained by Example 22. Then, 1.0 g (13 mmol) of lithium diethylamide $LiN(C_2H_5)_2$ was put into the flask, followed by stirring at room temperature for 1 hr. The resulting reaction liquid was subjected to a distillation at 125° C. under 0.12 kPa, thereby obtaining a distillate 24.5 g. This distillate was found by $^1HNMR$ to contain tetrakis (diethylamido)hafnium $Hf[N(C_2H_5)_2]_4$ as a main component. Furthermore, the zirconium concentration of the distillate was 0.7 wtppm. Furthermore, it was found that the methanesulfonic acid ion concentration of the distillate had decreased to 10 wtppm or less.

The residue after the distillation was in 1.3 g and had a zirconium concentration of 2.2 wtppm and a methanesulfonic acid ion concentration of 13.2 wt %.

The yield of the obtained high-purity tetrakis(diethylamido)hafnium, based on the crude tetrakis(diethylamido) hafnium having a zirconium concentration of 900 wtppm, was 52 wt %.

COMPARATIVE EXAMPLE

Example 1 was repeated except in that trifluoromethanesulfonic acid was not added. In fact, 10 g of a crude tetrakis(diethylamido)hafnium $Hf[N(C_2H_5)_2]_4$ having a zirconium concentration of 1,000 wtppm was subjected to a distillation at 125° C. under 0.12 kPa, thereby obtaining a distillate of 98 g. This distillate was found by $^1HNMR$ to contain tetrakis(diethylamido)hafnium $Hf[N(C_2H_5)_2]_4$ as a main component. Furthermore, the zirconium concentration of the distillate was found by ICP spectrometry to be 950 wtppm.

What is claimed is:

1. A process for producing a high-purity hafnium amide, comprising the steps of:
    (a) adding a compound which contains a carbonyl group or sulfonyl group and is represented by the formula of $A(O_yXO_nR_f)_m$, where A represents a hydrogen atom, oxygen atom or hafnium atom,
    where X represents a carbon atom or sulfur atom when A represents a hydrogen atom or oxygen atom,
    where X represents a sulfur atom when A represents a hafnium atom, where each of m, n and y represents 1 when A and X respectively represent a hydrogen atom and a carbon atom,
    where m, n and y respectively represent 1, 2 and 1 when A and X respectively represent a hydrogen atom and a sulfur atom,
    where m, n and y respectively represent 2, 1 and 0 when A represents an oxygen atom and when X represents a carbon atom,
    where m, n and y respectively represent 2, 2 and 0 when A represents an oxygen atom and when X represents a sulfur atom,
    where m, n and y respectively represent 4, 2 and 1 when A represents a hafnium atom,
    where $R_f$ is a $C_1$-$C_{12}$ alkyl group, $C_1$-$C_{12}$ perfluoroalkyl group, $C_6$-$C_{12}$ aryl group, or $C_4$-$C_{12}$ heteroaryl group, when A represents a hydrogen atom or oxygen atom, and
    where $R_f$ is a $C_1$-$C_{12}$ perfluoroalkyl group when A represents a hafnium atom,
    to a crude hafnium amide which is represented by the formula of $Hf[N(R_1)(R_2)]_4$, where each of $R_1$ and $R_2$ independently represents a methyl group or ethyl group, and which contains a zirconium component as an impurity; and
    (b) subjecting a product of the step (a) to a distillation under reduced pressure, thereby removing the zirconium component from the crude hafnium amide.

2. A process according to claim 1, further comprising the steps of:
    (c) adding a lithium alkylamide represented by the formula of $Li(NR_3R_4)$, where each of $R_3$ and $R_4$ independently represents a methyl group or ethyl group, to a distillate obtained by the step (b); and
    (d) subjecting a product of the step (c) to a distillation under reduced pressure.

3. A process according to claim 1, wherein the step (a) is repeated by adding the compound to a product of the step (b).

4. A process according to claim 1, wherein the crude hafnium amide is tetrakis(diethylamido)hafnium.

5. A process according to claim 1, wherein the compound of the step (a) is one selected from the group consisting of acetic acid, trifluoroacetic acid, benzoic acid, methanesulfonic acid, trifluoromethanesulfonic acid, benzenesulfonic acid, acetic anhydride, trifluoroacetic anhydride, benzoic anhydride, methanesulfonic anhydride, trifluoromethanesulfonic anhydride, benzenesulfonic anhydride, and hafnium trifluoromethanesulfonato.

6. A process according to claim 1, wherein the compound of the step (a) is one selected from the group consisting of trifluoromethanesulfonic acid, hafnium trifluoromethanesulfonato, trifluoromethanesulfonic anhydride, trifluoroacetic acid, methanesulfonic acid, benzenesulfonic acid, and methanesulfonic anhydride.

7. A process according to claim 1, wherein the compound of the step (a) is trifluoromethanesulfonic acid.

8. A process according to claim 1, wherein the distillation of the step (b) is conducted under a pressure of 0.01-0.60 kPa.

9. A process according to claim 2, wherein an alkyl substituent of the lithium alkylamide of the step (c), which is represented by the formula of $R_3R_4$, is identical with an alkyl substituent of the hafnium amide of the step (a), which is represented by the formula of $(R_1)(R_2)$.

10. A process according to claim 2, wherein the distillation of the step (d) is conducted under a pressure of 0.01-0.60 kPa.

* * * * *